United States Patent [19]

Knoch

[11] Patent Number: 5,461,695

[45] Date of Patent: Oct. 24, 1995

[54] NEBULIZING ASSEMBLY WITH HEATING EQUIPMENT

[75] Inventor: Martin Knoch, Berg, Germany

[73] Assignee: Paul Ritzau Pari-Werk GmbH, Germany

[21] Appl. No.: 97,053

[22] Filed: Jul. 27, 1993

[30] Foreign Application Priority Data

Aug. 5, 1992 [DE] Germany .......................... 42 25 928.2

[51] Int. Cl.$^6$ ..................................................... F24F 6/14
[52] U.S. Cl. ........................... 392/394; 392/404; 392/405
[58] Field of Search ............................ 392/394, 403, 392/404, 405, 406; 239/338; 128/200.14–200.23

[56] References Cited

U.S. PATENT DOCUMENTS

| | | | |
|---|---|---|---|
| 1,427,094 | 8/1922 | Daniel | 392/394 |
| 3,927,300 | 12/1975 | Wada | 338/55 |
| 4,291,838 | 9/1981 | Williams | 239/338 |
| 4,401,114 | 8/1983 | Lwoff | 128/200.14 |
| 4,911,157 | 3/1990 | Miller | 128/200.21 |
| 4,951,659 | 8/1990 | Weiler | 128/200.18 |
| 4,963,289 | 10/1990 | Ortiz | 239/338 |
| 5,063,921 | 11/1991 | Howe | 128/200.14 |
| 5,277,175 | 1/1994 | Riggs | 128/200.21 |

FOREIGN PATENT DOCUMENTS

| | | |
|---|---|---|
| 1683944 | 8/1953 | Germany . |
| 1060802 | 7/1959 | Germany . |
| 1898032 | 4/1964 | Germany . |
| 3043537 | 7/1982 | Germany . |

*Primary Examiner*—Teresa J. Walberg
*Attorney, Agent, or Firm*—Merchant, Gould, Smith, Edell, Welter & Schmidt

[57] ABSTRACT

An assembly for nebulizing, distributing and mixing liquid or powdered substances via a flow of compressed air, produces aerosols for inhalation purposes, with a nebulizing nozzle in a nebulizing chamber into which a supply chimney (21) extends so that air can enter. There is a heating assembly (30) in the supply chimney which warms the incoming air. Thus, the cooling effect which occurs during nebulization can be eliminated and an aerosol at a suitable temperature is delivered.

9 Claims, 3 Drawing Sheets

NEBULIZING ASSEMBLY WITH HEATING EQUIPMENT

FIELD OF THE INVENTION

The invention on hand concerns an assembly for nebulizing, distributing and mixing liquid or powder substances using a compressed air flow, especially for creating aerosols for inhalation purposes.

BACKGROUND OF THE INVENTION

Such an assembly is known from EP-A1-0 170 715. The known assembly consists of a container for the substance to be nebulized and a nebulizer cap which can be placed on the container with a co-axial air supply chimney through which air enters into the nebulizing chamber defined by the container and nebulizer cap. There is a nebulizing nozzle located centrally in the nebulizing chamber from whose nozzle head the gaseous compressed substance exits and which sucks the substance to be nebulized through the suction channels in the nozzle head and nebulizes it. The mouth of the nozzle is located across from where the end of the supply chimney enters the nebulizing chamber. During inhalation, the surrounding air flows through the supply chimney into the nebulization chamber and is inhaled by the patient together with the nebulized substance. A cooling effect occurs during the nebulization of the substance and during the mixing with the incoming surrounding air which is due mainly to evaporation. This lowers the temperature of the aerosol which the patient inhales.

A nebulizer is known from DE-A1-30 43 537 in which the substance to be nebulized is warmed up by an electric heating element. This is to prevent the strong cooling effect caused by the aerosol flow when it comes into contact with the mucus membranes. The electrical heating element of the known nebulizer is a PTC-thermistor which is in heat-conducting contact with the container for the substance to be nebulized and which is located in a body made of good heat-conducting material. In general, the known nebulizer works satisfactorily.

However, it was recognized that heating the substance to be nebulized also has disadvantages. On the one hand, an unfavorable influence on the aerosol spectrum occurs in that the distribution of the droplet spectrum is dependent on another variable, namely the temperature of the substance to be nebulized. On the other hand, overheating can occur during the warming of the substance to be nebulized, especially in the case of medications, since the requested temperature could be very high. The medication can be destroyed or damaged due to the occasional even only localized overheating. Furthermore, cooling occurs due to the mixing of the aerosol with the supplied ambient air which can either cancel the effect caused by the heating of the substance to be nebulized or which makes so much heating necessary that overheating can not be prevented.

SUMMARY OF THE INVENTION

Based on this, the invention has the task of making an assembly as mentioned at the beginning with which a warmed aerosol can be produced without the danger of overheating the substance to be nebulized.

The basic idea of the invention is to warm the aerosol indirectly by warming the entrained air. Especially in the case of inhalation devices with chimneys the entrained air can be warmed sufficiently and in a controlled manner since, due to the chimney, the entrained air undergoes a certain guidance and is channeled. By placing a suitably shaped heating assembly in the chimney, a negative effect on the flow conditions will, for the most part, be prevented. Specifically the distribution of the droplet sizes will not be affected by mixing nebulized substance and entrained air.

On the contrary, the solution as per the invention has the positive effect that the primary aerosol in the area of the nebulizing nozzle evaporates more because the entrained air has a higher temperature. This leads to an increased concentration in the droplets by which, at the same droplet spectrum transported by the air flow, a higher output rate of the substance to be nebulized is achieved. It was recognized that heating the aerosol, i.e., the entrained air/aerosol mixture, in the general area of the outlet connection leads to higher deposits of the nebulized substance and therefore to a reduction of the output rate. The cleaning problems which occur in the case of a direct heating of the aerosol are also avoided in the solution as per the invention.

An overheating of the nebulized substance does not occur in any case since the warming of the substance is only due to the contact with the warmed entrained air. The entrained air, however, is never heated to a temperature above about 50° C.

BRIEF DESCRIPTION OF THE DRAWINGS

In the following the invention is described in more detail based on applications with reference to the attached drawings that show:

FIG. 2, and FIG. 4: an inhalation device as per the invention in which the heating assembly is integrated in a specially designed chimney.

DETAILED DESCRIPTION OF THE PREFERRED EMBODIMENTS

Figure 1:
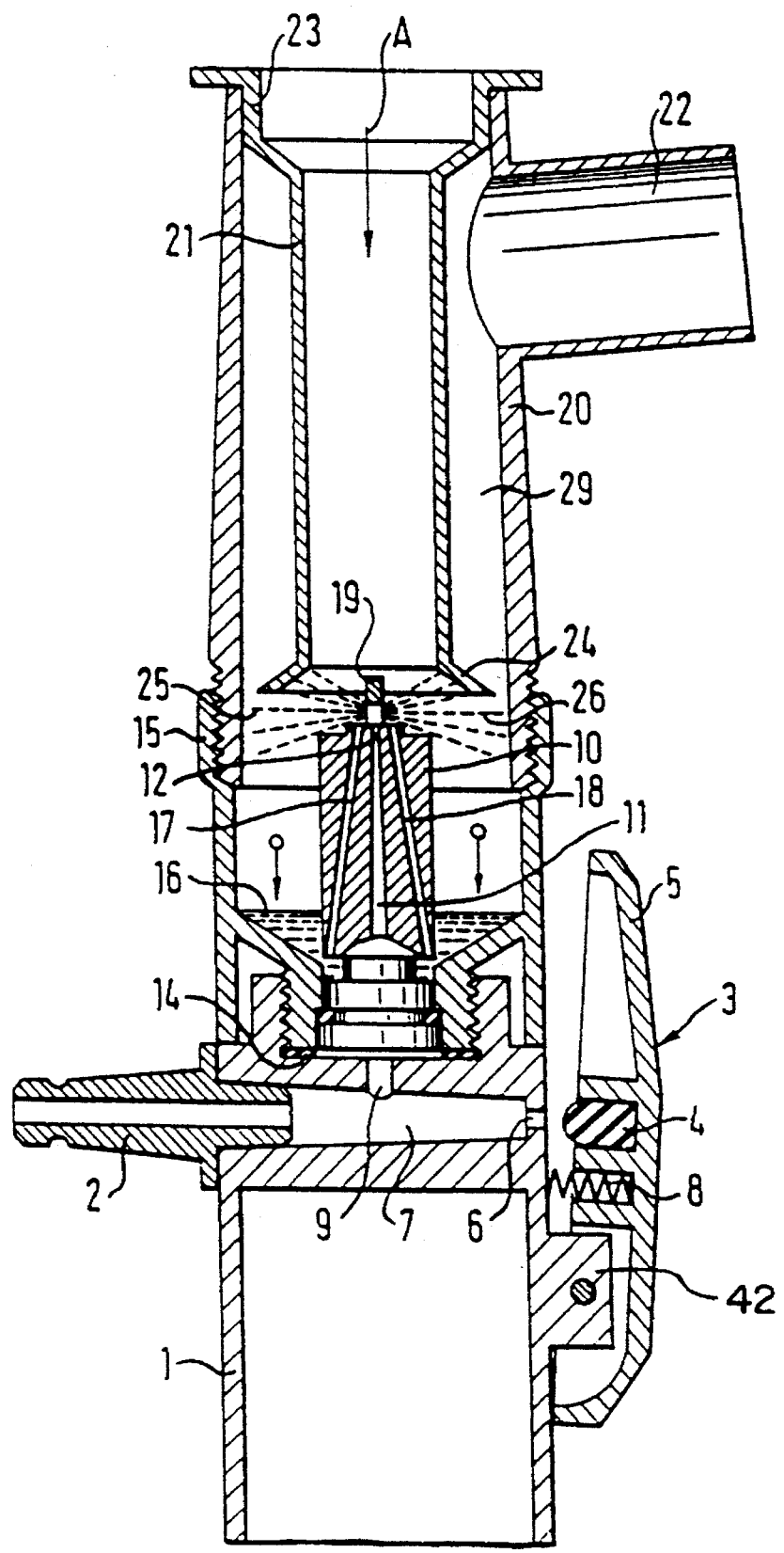
FIG. 1: a well-known inhalation device with chimney.

As an introduction, an inhalation device for treating the lungs and respiratory tract is to be described based on FIG. 1 onto which the heating assembly as per the invention can be fitted and which serves as an example for a nebulizing assembly.

The inhalation device shown in FIG. 1 includes a cylindrical nebulizer bottom part 1 with connecting piece 2 for the compressed air line and, positioned across from the connecting piece 2, the push lever 3 with a gasket insert 4 for sealing the outlet orifice 6 in the feed channel. The push lever is pivotally mounted on protrusion 42. The user can easily bring the push lever 3 from its "off" to its "on" position by pressing on the end 5 of the lever, to overcome the force of the spring 8, thereby bringing the front part of the push lever 3 into contact with the surface of the nebulizer whereby the gasket insert 4 is placed on the outlet orifice 6. This blocks the supply channel for the compressed air and detours it through the cross drill 9 to the central compressed air line 11 of the nozzle head 10.

The cylindrical container 15 for holding the substance to be nebulized is fastened, for example screwed on as shown in FIG. 1, on the nebulizer bottom part 1 in the known manner by interposing an elastic gasket ring 14. The nebulizing nozzle is also located in the container 15 and it consists of the nozzle head 10 with the central air line 11 and the bilaterally positioned suction channels 17 and 18 for the substance to be nebulized 16 and the air flow control 19. The central compressed air line 11 tapers toward the upper end of the nozzle head and ends in the narrow nozzle drilling 12 which opens at the nozzle head 10 below and across from the air flow control 19.

The cylindrical nebulizer cap 20 is fastened, for example screwed, as shown in FIG. 1, onto the container 15. The nebulizer cap 20 consists of a co-axial supply chimney 21 that extends into the interior of the inhalation device all the way to close above the air flow control 19. The aerosol outlet connection 22, onto which a mouthpiece which is not shown in the drawing can be mounted, is tip-stretched in the upper part of the nebulizer cap 20. The patient inhales the aerosol produced by the nebulizing nozzle through the aerosol outlet connection 22 whereby ambient air enters the inside of the inhalation device through the supply chimney in the direction of arrow A.

The supply chimney 21 has a baffle 24 at its lower end which further nebulizes at least a portion of the larger particles which were produced along the slanted surfaces of the air flow control 19. The baffle 24 also serves to cause particles which are too large to fall back into the container 15 to be renebulized.

A compressed air source (for example a compressor) which produces the necessary pressure of at least 0.6 bar is connected to the connection piece 2. The compressed air flows through the central compressed air line 11 and the nozzle drilling 12 to the outlet in the nozzle head 10 when the outlet of the feed channel 7 is closed by pressing the push lever 3. Thereby the substance to be nebulized is sucked from the lower area of the container 15 through the neighboring suction channels 17 and 18 and nebulized on the slanted impact surfaces of the air flow control 19 and distributed. The usual wedge angle of the air flow control 19 is about 120°, so that an aerosol fan 25 and 26 covering an angle range of 30° is formed on both sides of the air flow control 19.

As already mentioned at the beginning, a cooling effect occurs during the nebulization of liquids due to the evaporation particularly of the smallest droplets. This causes the temperature of the entire aerosol to fall considerably.

During inhalation, the patient sucks in the aerosol produced in this manner through the aerosol outlet 22 whereby the entrained air entering through the chimney 21 is mixed with the aerosol.

In the inhalation device shown in FIG. 1, the nebulizer cap 20 is open at the top and is closed by the supply chimney 21 which, in order to accomplish this, tapers to a insert cap 23 which is across from the baffle 24 and whose diameter is the same as that of the opening of the nebulizer cap 20 and which assures a secure and essentially air-tight fit of the supply chimney.

Figure 2:
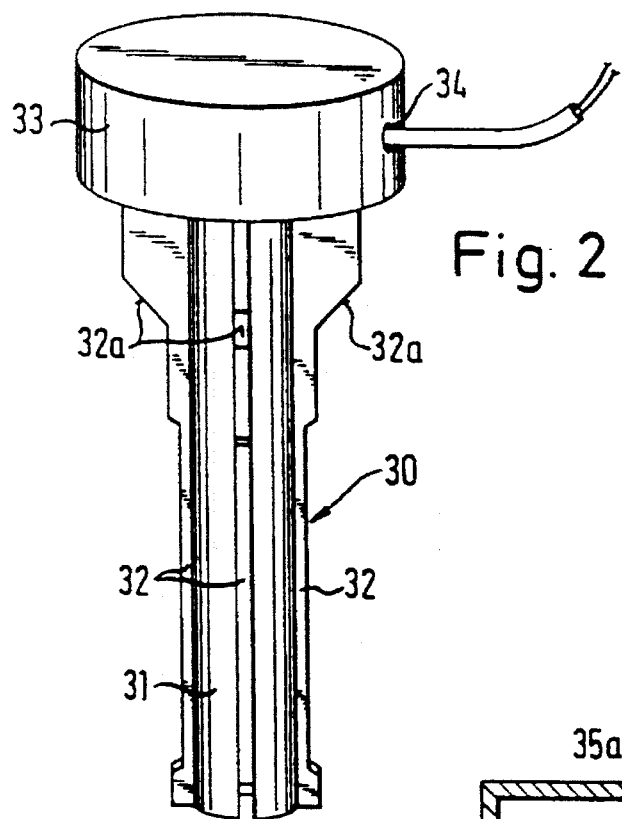
FIG. 2: a heating assembly as per the invention shown in perspective.

FIG. 2 shows a perspective view of a heating assembly 30 which warms the ambient air which enters through the supply chimney as per the invention. The heating assembly 30 includes a cylindrical core body 31 and many ribs 32 which extend radially out from the core body. The core body 31 and the ribs 32 are made of a good heat-conducting material, preferably aluminum, and made of one piece. The core body 31 has a thin wall and is closed at the lower end so that an electrical heating element can be placed inside. A terminal body 33 closes the core body 31 at its upper end. The terminal body 33 has the shape of a flat cylindrical disk whose cylinder axis is coaxial to the long axis of the core body 31. The diameter of the terminal body is so large that it overlaps the heat exchanger part of the heating element, which consists of the core body and the ribs, on all sides. Thus, the terminal body 33 can also serve as a handgrip for the heating element 30. There is an opening 34 on the side of the terminal body through which the electrical supply lines for the electrical heating element are placed.

Figure 3:
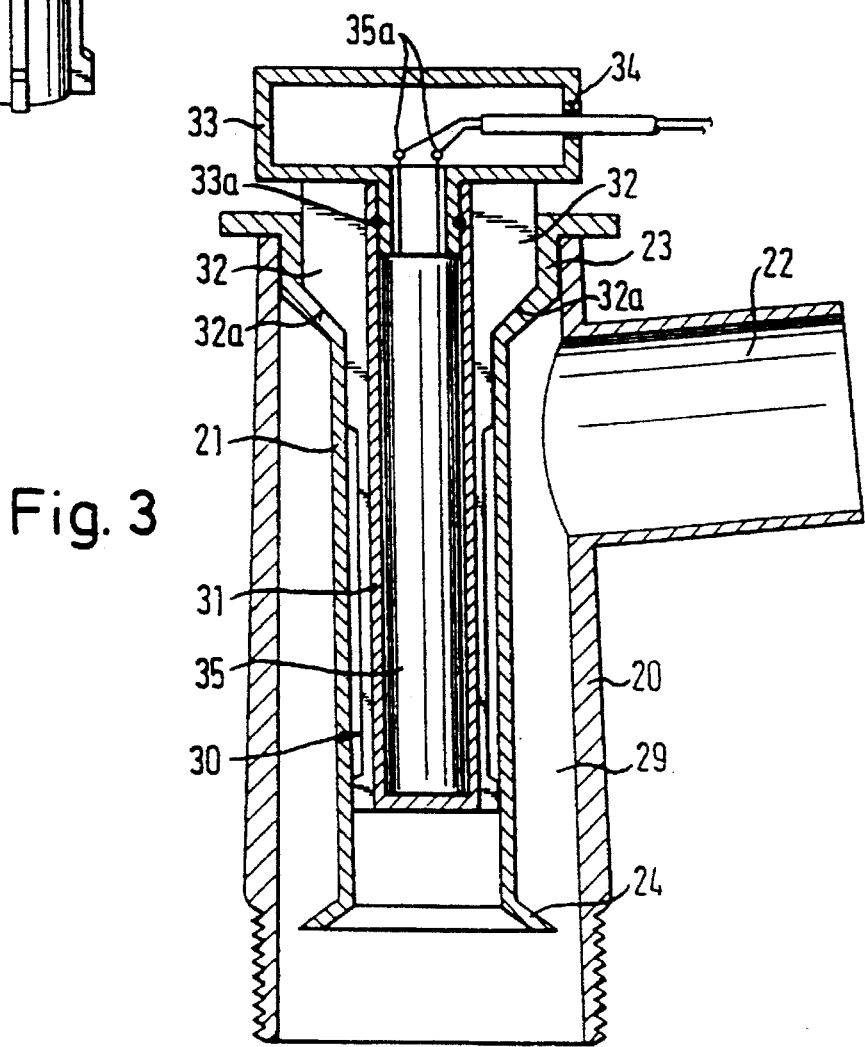
FIG. 3: a part of an inhalation device as per the invention which is equipped with a heating assembly as per

The ribs 32 of the heating element 30 are shaped in such a way that sloped contact surfaces 32a are formed on which the heating assembly 30 is placed on when it is placed in the supply chimney of the known inhalation device as is shown in FIG. 3. The shape of the contact surfaces 32a corresponds essentially to the tapered part of the insert cap 23 of the supply chimney.

The contact surfaces 32a of the ribs 32 change into a segment in which the ribs 32 have a constant height which is chosen such the distance between the outer surfaces corresponds to the diameter of the supply chimney. A segment in which the ribs have a low height links onto this segment so that there is a gap between the outer surface of the ribs and the supply chimney as can be seen in FIG. 3. At the lower end the ribs 32 have another short segment where the height of the ribs was chosen such that the outer surfaces of the ribs are spaced at a distance which corresponds to the diameter of the supply chimney 21.

FIG. 3 shows only the nebulizer cap 20 of the inhalation device shown in FIG. 1 as well as the therein used supply chimney 21. The heating assembly as per the invention is placed in the supply chimney in such a manner that heat exchanger contacts the contact surfaces 32a along the conical segment of the insert cap 23 of the supply chimney. The heat exchanger extends close to the baffle 24 in the supply chimney 21, i.e., close to the nebulizer nozzle. Furthermore, the heat exchanger projects out of the top of the supply chimney. Thus the ambient air can pass by the ribs 32 through the supply chimney 21 when the patient inhales the aerosol through the aerosol outlet 22. Since the ambient air flows through the heat exchanger it is warmed so that warm ambient air arrives at the lower end of the supply chimney 21 and is ready for mixing with the nebulized substance.

In the cut view of FIG. 3 one can see that an electrical heating element 35 is provided for in the interior of the heat exchanger which is in contact with the closed end of the core body 31 at the one end and which is clamped by the terminal body 33 at the other end. For this the terminal body 33 has a cylindrical insert piece whose diameter was chosen such that it can be placed in the cylindrical opening of the core body 31. A firm fit is insured either by choosing the suitable diameter of the inserted piece or by placing an elastic sealing ring 33a between the inserted piece and the core body. As shown in FIG. 3a groove along the entire circumference of the inserted piece in which the sealing ring is placed is meant for just this.

The terminal piece 33 and the inserted piece are either hollow or have at least a passage which makes it possible to insert the electrical supply lines from the opening 34 to the electrical connections 35a of the electrical heating element 35.

Since the terminal piece 33 extends over the heat exchanger 30 on all sides, a gap is formed between the upper end of the supply chimney and the bottom surface of the terminal piece 33 when it is inserted through which the ambient air can enter the supply chimney. Since the ribs 32 of the heat exchanger are shifted toward the inside, as can be seen in FIG. 3, an inadvertent contact with the heated ribs even in the area outside the supply chimney is not possible.

The electrical heating element 35 has mainly a PTC resistor (cold conductor) whose electrical resistance increases with increasing temperature. Therefore one can tune the PTC resistor and its voltage source in such a manner that a certain operating temperature is reached by self-regulation. In order to reach an aerosol temperature at the aerosol outlet 22 of about 28° C. to 32° C., the temperature of the electrical PTC heating element should be between 150° C. and 170° C. and the power consumption through the PTC heat resistor should be between 10 and 15 watts. Then the temperature at the surface of the heat exchanger lies between 130° C. and 150° C. which is sufficient to heat the ambient air to the desired temperature. Higher aerosol temperatures for the therapy of the upper respiratory tract can be reached using heating elements with more power consumption at a temperature of up to 220° C. and a power absorption of up to 36 watts.

The temperature of the aerosol should be between 25° C. and 40° C., preferably between 28° C. and 37° C.

A conventional plug power supply with an initial voltage of about 12 volt is sufficient as the voltage supply for the electrical PTC heat resistor.

Figure 4:
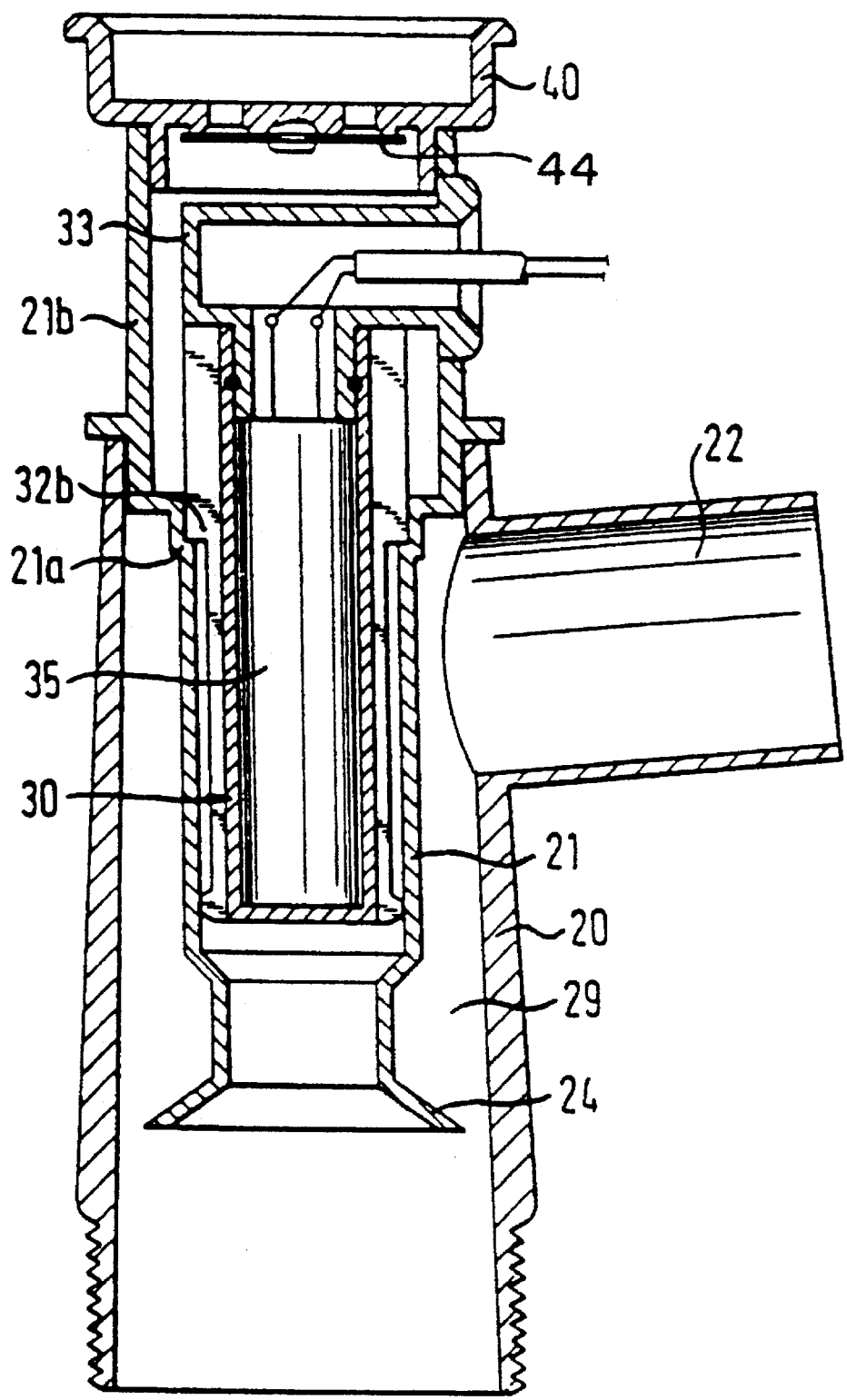

FIG. 4 shows another example in which the heating assembly 30 is connected firmly with the supply chimney 21. In this example the heating element also consists of a heat exchanger and an electrical heating element 35 inside whereby the heat exchanger is comprised of a cylindrical core body and radially extending ribs. However, the ribs do not have sloped contact surfaces since the supply chimney is adapted to the heating assembly.

As shown in FIG. 4, a protruding edge 32b of the ribs of the heat exchanger are positioned on a ledge 21a located along the circumference of the inner wall of the supply chimney 21. The height of the ribs of the heat exchanger were chosen such that the outer surfaces of the ribs are spaced at a distance corresponding to the diameter of the supply chimney 21 immediately above the ledge. Continuing on to the closed end of the core body the ribs have a height which is less so that the outer surfaces of the ribs do not come into contact with the supply chimney. Not until the end of the heat exchanger is the height of the ribs slightly larger so that, in this area, the outer surfaces of the ribs come into contact with the inner wall of the supply chimney as can be seen in FIG. 4. The heat exchanger is thereby fitted securely in the supply chimney.

In contrast to conventional supply chimneys a cylindrical part 21b into which the heat exchanger of the heating assembly 30 projects is attached to the upper end. However, the cylindrical part 21b protrudes over the heat exchanger so that inadvertent contact with the warm heat exchanger is not possible. In this example the terminal piece 33 of the heating assembly has a smaller diameter so that the ambient air can flow through the cylindrical part, past the ribs of the heat exchanger into the supply chimney 21. Essentially, the diameter of the terminal piece corresponds to the distance between the outer surfaces of the opposing ribs of the heat exchanger. This insures that one cannot touch through the upper opening of the heat exchanger but there is sufficient flow of ambient air for inhalation. Since the supply chimney 21 and heating assembly 30 are set up as a unit in this example, the terminal piece 33 is in contact with the cylindrical part 21b which is an extension of the supply chimney 21 at its upper end. The electrical connection lines pass through the outer cylindrical part 21b of the supply chimney and the terminal body 33.

The extended part 21b of the supply chimney protrudes a little over the terminal body 33 of the heating assembly so that there is an opening above the terminal body 33 whose diameter corresponds to the diameter of the opening of the insert cap 23 of the supply chimney shown in FIG. 1. A valve element 40 provided with valve 44 can be inserted in this opening which, in the conventional inhalation device, is inserted in the opening of the insert cap 23 of the supply chimney. The extension of the supply chimney 21 over the terminal body 23 of the heating assembly makes it possible to use this valve element with a supply chimney which is depicted as a unit with the heating assembly 30 as per this example. Furthermore, the heating assembly of this example as per FIG. 4 corresponds to the set-up which is described together with FIG. 2 and 3. In this example the ambient air flows passed the ribs and the core body of the heat exchanger through the supply chimney and is thereby heated. The temperatures required for this are not different from those of the first example.

Another possibility for temperature regulation is offered by this invention in so far as a conventional electrical heating element is provided for in the heat exchanger part of the heating assembly and a temperature sensor is placed in the aerosol outlet 22 which measures the temperature of the aerosol that the patient inhales. Based on the recorded temperature, the heating performance of the conventional electrical heating element can then be adapted accordingly. This is beneficial in that it is a controlled control circuit which falls back on the temperature in a certain range which should be between 28° and 32° C. namely the range of the aerosol inhaled by the patient. Despite the more elaborate switching technology, this type of temperature regulation can be advantageous in some cases.

In order to achieve an optimal heat transfer from the heating element to the heat exchanger part of the heating assembly, the heating element is preferably adapted to the inner diameter of the core body of the heat exchanger and its outer surfaces lies firmly on the inner surfaces of the core body. The core body preferably has thin walls whereas the ribs of the heat exchanger should have a certain thickness in order to transfer the heat better.

What is claimed is:

1. A device for producing aerosol for inhalation purposes by mixing a liquid or powdered substance with a flow of gas from a compressed gas source, the device comprising:

a nebulizing chamber for containing a liquid or powdered substance to be nebulized;

a nebulizing nozzle located in the nebulizing chamber;

means for supplying gas from a compressed gas source to the nebulizing nozzle, the nebulizing nozzle being capable of mixing the liquid or powdered substance with gas from the compressed gas source to nebulize the liquid or powdered substance;

a supply chimney in fluid communication with the nebulizing chamber, for permitting the entry of ambient air into the nebulizing chamber; and a heating assembly disposed in the supply chimney for heating ambient air passing through the supply chimney before the ambient air enters the nebulizing chamber, the nebulizing nozzle being located outside the supply chimney.

2. The device of claim 1, wherein the heating assembly has an electrical heating element.

3. The device of claim 2, wherein the electrical heating element is a PTC resistor.

4. The device of claim 1, wherein the heating assembly is comprised of a heat exchanger and a terminal body.

5. The device of claim 4, wherein the heat exchanger includes a cylindrical core part and a plurality of ribs which extend radially from the cylindrical core body.

6. The device of claim 5, wherein the ribs have contact surfaces that are sloped with respect to a lengthwise axis of the cylindrical core body on which the heating assembly rests in the area of a conical insert cap of the supply chimney.

7. The device of claim 5, wherein the heat exchanger extends out of the supply chimney and the terminal body projects out of the heat exchanger on all sides so that an inadvertent touching of the heat exchanger is prevented.

8. The device of claim 5, wherein the heating assembly and supply chimney are a single unit.

9. The device of claim 8, wherein the supply chimney has a cylindrical part that surrounds a protecting part of the heat exchanger.

* * * * *